United States Patent [19]
Wilkins et al.

[11] Patent Number: 5,518,878
[45] Date of Patent: May 21, 1996

[54] CRYOPRESERVATION OF CULTURED SKIN OR CORNEA EQUIVALENTS WITH AGITATION

[75] Inventors: Leon M. Wilkins; Stephen R. Watson, both of Canton, Mass.

[73] Assignee: Organogenesis Inc., Canton, Mass.

[21] Appl. No.: 121,377

[22] Filed: Sep. 15, 1993

[51] Int. Cl.$^6$ ..................................................... A01N 1/02
[52] U.S. Cl. ................................................................ 435/1.3
[58] Field of Search ...................................... 435/1

[56] References Cited

U.S. PATENT DOCUMENTS

| | | | |
|---|---|---|---|
| 4,485,096 | 11/1984 | Bell | 424/95 |
| 4,485,097 | 11/1984 | Bell | 424/95 |
| 4,539,716 | 9/1985 | Bell | 623/1 |
| 4,546,500 | 10/1985 | Bell | 623/1 |
| 4,604,346 | 8/1986 | Bell | 435/1 |
| 4,837,379 | 6/1989 | Weinberg | 424/101 |
| 5,084,377 | 1/1992 | Rowan et al. | 435/1 |
| 5,145,770 | 9/1992 | Tubo et al. | 435/1 |

OTHER PUBLICATIONS

Madden et al, Cryobiology, vol. 30, issued 1993 "The Effect of Polyvinylpyrrolidone and the Cooling Rate during Corneal Cryopreservation", pp. 135–137.
Delbosc, et al, Journal of French Ophtalmology, vol. 7, No. 4, issued 1984, "la cryoconservation corneenne chez l'homme: proposition technique originale", pp. 321–331.
Johnstone, et al, Cornea, vol. 11, No. 3, issued 1992, "Cryopreservation of Rabbit and Cat Corneas", pp. 211–220.
Armitage, et al, Cryobiology, vol. 27, issued 1990, "Vitrification of Organized Tissues", pp. 483–491.
Fahy et al., "Vitrification as an approach to cryopreservation," Cryobiology 21:407–426 (1984).
Takahashi et al., "Vitrification of Human Monocytes," Cryobiology, 23:103–115 (1986).
Parenteau et al., "Epidermis Generated in Vitro: Practical Considerations and Applications," J. of Cellular Biochemistry, 45:245–251 (1991).
Parenteau et al., "The Organotypic Culture of Human Skin Keratinocytes and Fibroblasts to Achieve from and Function," Cytotechnology, 9:163–171 (1992).
Bell et al., "The Living Skin Equivalent: Its Organotypic Properties and Its Responses to Irritants," Toxic In Vitro, 5:591–596 (1991).
Hubel et al., "Intercellular Ice Formation During the Freezing of Hepatocytes Cultured in Double Collagen Gel," Biotechnology Program, 7:554–559 (1991).
Gay et al., "The Living Skin Equivalent as a Model In Vitro for Ranking the Toxic Potential of Dermal Irritants," Toxic In Vitro, 6:303–315 (1992).
Rall, W. F., "Factors Affecting the Survival of Mouse Embryos Cryopreserved by Vitrification," Cryobiology, 24:387–402 (1987).

Primary Examiner—Marian C. Knode
Assistant Examiner—S. Saucier
Attorney, Agent, or Firm—Hale and Dorr

[57] ABSTRACT

This invention is directed to cryopreservation of cultured tissue equivalents made by in vitro technology. The invention involves immersing a cultured tissue equivalent in a cooled cryoprotectant solution, agitating the cryoprotectant solution and the immersed cultured tissue to achieve effective penetration of the cryoprotectant solution into the cultured tissue equivalent, and then freezing the cultured tissue at a high freezing rate. The cryopreserved cultured tissue equivalent may be stored for indefinite periods of time prior to use. The cultured tissue equivalent is an in vitro model of the equivalent human tissue, which, when retrieved from storage can be used for transplantation or implantation in vivo or for screening compounds in vitro.

16 Claims, 6 Drawing Sheets

CRYOPRESERVATION OF CULTURED SKIN OR CORNEA EQUIVALENTS WITH AGITATION

FIELD OF THE INVENTION

This invention is directed to cryopreservation of cultured tissue equivalents made by in vitro technology. The cryopreserved cultured tissue may be stored for indefinite periods of time prior to use. The cultured tissue is an in vitro model of the equivalent human tissue, which, when retrieved from storage can be used for transplantation or implantation in vivo or for screening compounds in vitro.

BACKGROUND OF THE INVENTION

Tissue culture techniques are being used in developing tissue and organ equivalents. These techniques involve collagen matrix structures which are capable of being remodeled into functional tissue and organs by the right combination of living cells, nutrients, and culturing conditions.

Currently the use of cultured tissue equivalents is restricted because such equivalents have a limited shelf-life. Thus, at present it is impossible to maintain a proper inventory for any length of time. Further, because of the limited shelf-life of the equivalents, there is a high degree of waste. Accordingly, the development of a successful cryopreservation method which would extend the length of time that the cultured tissues could be stored so that a proper inventory could be maintained, and which would substantially reduce waste, is desirable. Such a cryopreservation method would enable the commercial use of such equivalents since an inventory of larger batch sizes could be maintained and quality control inspected. Currently, USP standards mandate sterility testing which requires 14 days. An additional advantage to developing a successful cryopreservation method is that it would enable one to arrest the growth of the cultured tissue equivalent at specific stages of development for further testing and analysis.

Currently, the storage time of biological materials is extended by freezing. The solidification of a liquid by freezing can take place as crystallization, involving an orderly arrangement of molecules. Alternatively, freezing can take place as amorphization or vitrification, a solidification without such an orderly arrangement.

Freezing living cells by crystallization is problematic in that intracellular ice crystals are formed. These ice crystals are detrimental to cell viability upon thawing. The cells could survive solidification and thawing, however, if they are cryopreserved by vitrification. Vitrification involves cooling and warming cells at controlled rates while the cells are immersed in cryoprotectants.

Fahy et al., "Vitrification as an approach to cryopreservation," *Cryobiology* 21:407–426 (1984), developed a cryoprotectant solution containing dimethyl sulfoxide (DMSO) and polymers which vitrified at 1 atmosphere. This cryopreservation medium was modified for the vitrification of human monocytes. Takahashi et al., "Vitrification of Human Monocytes," *Cryobiology* 23:103–115 (1986).

Vitrification of cells and tissues using cryoprotectants is problematic in that cell viability is low upon thawing because the cells cannot tolerate the highly concentrated cryoprotectant solutions used, the high rates of cooling and warming, thermal shock, and ice formation during warming or devitrification. Using prior art methods, it is not possible to cryopreserve a cultured tissue equivalent, in part because it is relatively thick and very heterogeneous. The present inventors have discovered that the same cryopreservation approach cannot be applied to all tissues. Thus, at present there is a strong need for an effective and commercially practical method of cyropreservation for cultured tissue equivalents.

SUMMARY OF THE INVENTION

The present invention provides a method for the successful preservation of cultured tissue equivalents at very low temperatures which avoids the formation of ice crystals, minimizes the effective concentration of potentially harmful chemicals, and permits the rapid introduction and removal of cryoprotectants at feasible temperatures, without the necessity of elaborate equipment to monitor precise conditions of concentration and temperature.

The inventors have discovered a method for cryopreserving cultured tissue equivalents made from in vitro techniques so that the tissues maintain their viability and utility as equivalents of human tissues. The invention includes the use of agitation to enhance the penetration of an effective amount of cryoprotectant. The present method allows the cryopreservation of cultured tissue equivalents in a manner which protects structural integrity and cellular viability.

The method of this invention involves the following steps: 1) immersing cultured tissue equivalent in a cooled cryoprotectant solution, agitating the cryoprotectant solution and the immersed cultured tissue to achieve effective penetration of the cryoprotectant solution into the cultured tissue equivalent and 2) freezing the cultured tissue at a high freezing rate to a temperature at or below at least about $-110°$ C., more preferably at or below $-140°$ C., and most preferably, at $-196°$ C.

Once frozen, the cultured tissue equivalent can be stored for indefinite time periods at a temperature of $-196°$ C., the temperature of liquid nitrogen.

Thawing the cryopreserved tissue equivalent is accomplished by warming the frozen tissue at a high rate of temperature increase, which is done in about 1 to 3 seconds. The frozen cultured tissue equivalent may be thawed in an aqueous bath at 37° C. or by another rapid heating mechanism.

Prior to use as an equivalent for human tissue, the thawed cultured tissue equivalent is rinsed to remove the cryoprotectant solution. The cryoprotectant solution may be removed by rinsing with, for example, an isotonic buffer solution at physiological pH. The cultured tissue equivalents can then be stored temporarily in such a buffer solution before use.

BRIEF DESCRIPTION OF THE FIGURES

FIG. 2 is a graph of viability testing of cryopreserved cultured tissue using the MTT assay.

FIG. 3 shows animal grafting of cryopreserved Living Skin Equivalents (LSE). FIG. 3(A) is the non-frozen, non-grafted control LSE (magnification=135×); FIG. 3(B) is the cryopreserved LSE 6 days after grafting (magnification=175×); FIG. 3(C) is the cryopreserved LSE 30 days after grafting (magnification=130×).

DETAILED DESCRIPTION OF THE INVENTION

Figure 1A:
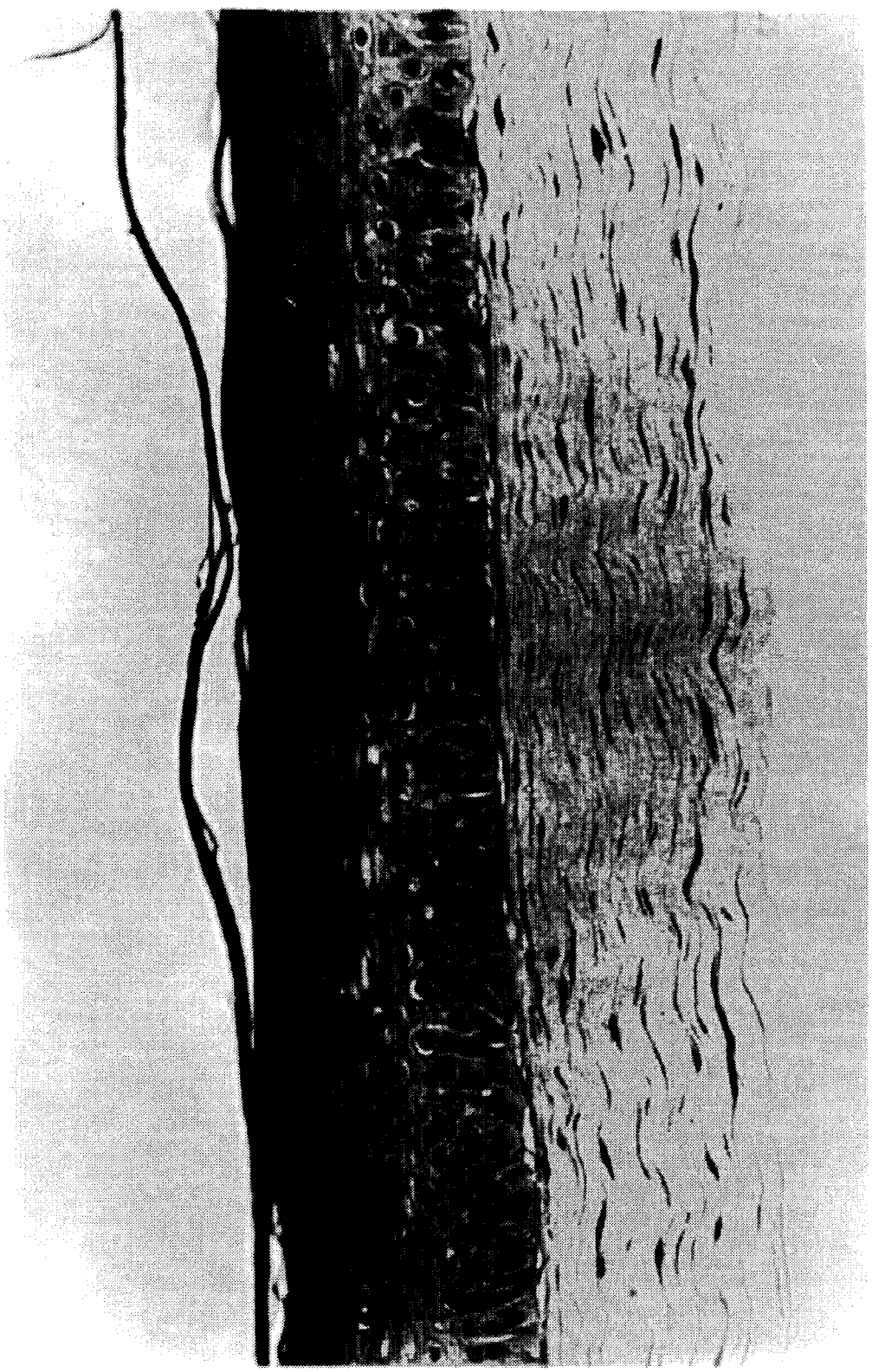
FIG. 1(A) is a cross section of a Living Skin Equivalent (LSE) after cryopreservation according to the methods described herein compared with FIG. 1(B) a cross section of an unfrozen LSE Control.

Tissue engineering is an emerging area which utilizes cultured tissue cells to construct tissue equivalents which can be used to examine the response to injury by chemical agents or pharmaceutical compounds. The cultured tissue may also be used to form graftable human tissue.

Tissue equivalents have been described extensively in many patents, including U.S. Pat. Nos. 4,485,096; 4,485,097; 4,539,716; 4,546,500; 4,604,346; and 4,837,379, all of which are incorporated herein by reference. One successful application of the tissue equivalent is called the "Living Skin Equivalent," which has a morphology similar to actual human skin. The Living Skin Equivalent (LSE) is composed of two layers: the upper portion is made of differentiated and stratified human epidermal keratinocytes that cover a lower layer of human dermal fibroblasts in a collagen matrix. Parenteau, et al., "Epidermis Generated In Vitro: Practical Considerations and Applications," *J. of Cellular Biochemistry*, 45:245–251 (1991); Parenteau, et al., "The organotypic culture of human skin keratinocytes and fibroblasts to achieve form and function," *Cytotechnology*, 9:163–171 (1992); and Bell et al., "The Living Skin Equivalent: Its Manufacture, Its Organotypic Properties and Its Responses to Irritants," *Toxic. in Vitro*, 5:591–596 (1991). LSE for graft is currently under investigation in clinical trials for three indications: venous ulcer, dermatological surgery, and burns. The LSE is a full-thickness, bilayered, in vitro engineered skin tissue.

An in vitro organ equivalent of the cornea of the eye has been developed as described in U.S. patent application serial number 07/974,740; now U.S. Pat. No. 5,374,515 incorporated herein by reference. The cornea tissue equivalent has three distinct cell layers, the external layer, a stratified squamous epithelium, the middle layer of collagen fibers and stromal cells, and an inner layer, simple squamous epithelium, also called the corneal endothelium. An in vitro cornea equivalent can be used for in vitro toxicity assays to serve as accurate and inexpensive non-animal predictive models of in vivo ocular and dermal irritation potential for many types of products and raw materials.

The goal of cryopreservation is to preserve the structural integrity and viability of biological materials for an indefinite period of time so that these materials can be available and used as needed. Complex tissues of finite life span will require cryopreservation to expand product availability and utility. The history of cryopreservation of biological material, however, has shown that the optimization of a cryopreservation protocol for a particular cell does not necessarily give good results when used with another cell type or with other cells in a tissue. The bilayered LSE required the development of more specialized methods due to the differences in cell density, water content and level of structural organization of the full-thickness LSE The cryopreservation protocols of this invention are also applicable to the trilayered cornea equivalent and other similarly structurally complex cultured tissue equivalents.

I. DEFINITIONS

As used herein, the term "cultured tissue equivalents" means tissue equivalents of mammalian tissues, wherein the tissue equivalents are made by in vitro techniques and are meant to include bilayered skin equivalents, particularly LSE, and trilayered cornea equivalents. The morphology of the cultured tissue equivalents are similar to the in vivo mammalian organ, typically the human organ. For illustration, the morphology of the LSE bears many similarities to human skin. Metabolically and mitotically active human dermal fibroblasts (HDF) are found throughout the dermal layer of the construct, and have been shown to secrete collagen and other matrix components into the lattice. The epidermis consists of a basal layer shown to divide with a mitotic rate similar to that of human skin. The suprabasal epidermis shows the same strata as skin in vivo, with well defined spinous and granular layers containing keratohyalin and lamellar granules covered by a stratum corneum. Immunohistochemistry demonstrates the presence of extracellular matrix components routinely fond at the dermo-epidermal junction in normal human skin, such as laminin, Type IV collagen and kalanin (GB3).

By use of the term "agitation" is meant any mechanical means of agitation to enhance perfusion of the cryoprotectant solution into the tissue equivalent, including centrifugation and shaking.

By the terminology "cryoprotectant solution" is intended any solutions which contain one or more cell-penetrating, glass-forming agents and/or one or more non-cell penetrating glass forming agent or any combination thereof. Non cell-penetrating, glass-forming agents include high molecular weight forms of complex carbohydrates, such as chondroitin sulfate, polyvinylpyrrolidone, polyethylene glycol or hetastarch, such as hydroxyethyl starch. The cell-penetrating, glass-forming agent is preferably glycerol, but may include propylene glycol, ethylene glycol, dimethylsulfoxide, and other penetrating glass forming agents known in the art.

Suitable cryoprotectant solutions for use in the present invention include both cell-penetrating, glass-forming agents and non cell-penetrating, glass-forming agents. The preferred cryoprotectant solution contains 65% glycerol in a base of Dulbecco's Modified Eagle's Medium (DMEM) + 0.3% newborn calf serum (NCS). Another suitable cryoprotectant solution for use in the present invention is 20.5% dimethyl sulfoxide (DMSO), 15.5% acetamide, 10.0% propylene glycol, 6.0% polyethylene glycol (PEG) in a base of 0.3% newborn calf serum (NCS) in Dulbecco's Modified Eagle's Medium (DMEM). These solutions can be modified and optimized by one of skill in the art using known cryoprotectants and freezing, storing, thawing, and rinsing procedures that are compatible with maintaining maximal viability, depending on the particular application.

II. CRYOPRESERVATION

The present cryopreservation method requires the immersion of the cultured tissue equivalent in cryoprotectant solutions for a period of time under conditions sufficient to permit the equilibration of the cells with the cryoprotectant.

The cultured tissue equivalent is serially immersed in a graded series of cryprotectant solutions of increasing concentration and decreasing temperature. Full strength (100% concentration) cryoprotectant solution is diluted with a base media to produce a series of lower concentration strengths. Suitable base media includes any known mammalian cell culture media used by those skilled in the art, and includes for example, Dulbecco's Modified Eagle's Medium. Prior to immersion, the series of cryoprotectant solutions are precooled. Preferably, the cultured tissue equivalent is first immersed in a 15% to 35% concentration cryoprotectant solution, more preferably 25% concentration, at 22° to 25° C., more preferably at room temperature. Next, the cultured tissue equivalent is immersed in a 40% to 60% concentration cryoprotectant solution, more preferably 50% concentration, at 10° to –2° C., more preferably at 4° C. Lastly, the cultured tissue equivalent is then immersed in a 100% concentration of cryoprotectant solution at –10° to –30° C., preferably –20° C. For each of these immersions, the cultured tissue equivalent is immersed in the specific solution for a time period of from about 10 to about 20 minutes, more preferably for about 15 minutes. The excess cryoprotectant solution from each immersion step is removed before the addition of a cooler, higher concentration cryoprotectant solution.

During any one or more of the immersion steps, preferably at the last immersion step utilizing 100% concentration of cryoprotectant solution, the cultured tissue equivalent in cryoprotectant solution is agitated for a time period sufficient to allow the effective permeation of the cryoprotectant into the cultured tissue equivalent. One of ordinary skill in the art can readily determine suitable lengths of time needed for agitation to achieve penetration of the cultured tissue based on factors which include for example, the type of cultured tissue equivalent, the amount and composition of the cryopreservation solution, and the force generated during agitation. Preferably, agitation is carried out for a time period of from about 10 to 20 minutes. Further, such agitation is preferably carried out utilizing a conventional shaker tray.

After the last immersion step, the cultured tissue equivalent and the cryoprotectant solution are cooled to at least about –140° C. to about –180° C. The cooling rate is preferably from about –10° C. per minute to about –30° C. per minute, more preferably from about –15° C. per minute to about –20° C. per minute. The cooling can be accomplished using a cooling device, including for example, a commercial programmable cell freezer which can be programmed to a temperature of from –110° C. to –196° C., more preferably from –140° C. to –180° C.

The resultant cryopreserved cultured tissue equivalent is then stored for example in a bag or plastic tray, at or below the glass transition temperature of approximately –110° C. Preferably the perfused cultured tissue equivalent is vacuumed sealed in a plastic pouch prior to freezing. It is desirable to vacuum seal the tissue equivalent because this procedure allows the rapid thawing of the material after immersion in a 37° C. water bath. Further, vacuum sealing allows the cultured tissue equivalent to be stored and thawed under sterile conditions and enhances rapid heat transfer during freezing and thawing. The cryopreserved cultured tissue equivalent can be vacuum sealed using conventional equipment and appropriate plastic bags both of which are readily available.

III. THAWING THE FROZEN CRYOPRESERVED CULTURED TISSUE EQUIVALENT

The frozen cultured tissue equivalent is thawed by warming it at a high rate of temperature increase such that the tissue is thawed in about from 1 to 3 seconds. Suitable methods for warming frozen cultured tissue equivalent at an extremely high thawing rate, include warming using a water bath or warming using induction heating. Preferably, the frozen cultured tissue equivalent is thawed by immersing the vacuumed sealed frozen cultured tissue equivalent in a water bath at a temperature of 37° C.

Due to the toxic nature of the cryoprotectant agents, tile cryoprotectant solution is removed from the thawed cultured tissue within about 15 minutes after thawing, preferably as soon as possible after thawing, to avoid damaging the viability of the cultured tissue. Once the cultured tissue is thawed, the cryoprotectant solution is replaced with an isotonic buffer solution at physiological pH (about 6.8 to 7.4 pH), preferably including 0.5 to 2.0 M sucrose.

A cultured tissue equivalent prepared as disclosed above may be used for transplantation or implantation in vivo or for screening compounds in vitro.

The following examples further describe the materials and methods used in carrying out the invention. The examples are not intended to limit the invention in any manner.

EXAMPLES

After trying several routine prior art protocols for cryopreservation of cultured tissue equivalent, living skin equivalent (LSE), without successful recovery of viability, it was determined that the high level of epidermal organization in LSE was limiting the ability to achieve cryopreservation using conventional methods. It appeared that in cryopreservation, the LSE acted more like tissue than a single cell suspension. The inventors then explored cryopreservation protocols based on the prior art concept of vitrification.

I. Freezing LSE by Classic Vitrification

Vitrification is a process of cryopreservation which utilizes increasing viscosity during cooling of a liquid to achieve the glass forming phase of solidification rather than the formation of crystals. Vitrification can be accomplished by dropping the temperature at a rate fast enough to prevent ice crystals from forming, using conventional freezing solutions, or by increasing the level of cryoprotectants to a level sufficient to prevent ice crystals from forming during conventional freezing rates.

It is believed that slow freeze protocols, typically using a cooling rate of 1° C./minute and a 5% to 20% concentration of cryoprotectant, achieve intracellular vitrification such that single cell suspensions are able to survive controlled extracellular ice crystal formation. (Hubel et al., "Intracellular Ice Formation during the Freezing of Hepatocytes Cultured in a Double Collagen Gel," *Biotechnol. Prog.*, 7:554–559 (1991). It has now been determined that complex, multilayered tissues with heterogeneous physical properties and different cell types in the layers are damaged during slow freeze protocols by ice formation. The three dimensional structure of a cultured tissue equivalent, as defined herein, makes it susceptible to intracellular ice formation and to extracellular ice formation.

The first vitrification solution tested was unsuccessful and exhibited a very high level of variability. This solution was modified VS1 (Fahy, et al., supra). The modified VS1 solution used in these tests contained 20.5% dimethylsulfoxide (DMSO), 15.5% acetamide, 10.0% propylene glycol, 6.0% polyethylene glycol (PEG) in a base of 0.3% newborn calf serum (NCS) in Dulbecco's Modified Eagle's Medium (DMEM). VS1 was modified to include the use of DMEM as a base media and the use of NCS instead of serum albumin.

Dilutions of the full strength modified VS1 solution were made with base media to achieve 50% and 25% strength solutions. The step wise addition protocol was as follows: LSE was immersed in 25% VS1 at room temperature for 15 minutes, then replaced with 50% VS1 at 4.0° C. for 15 minutes, then replaced with 100% VS1 at −20° C. for 15 to 20 minutes. The LSE was then placed into a −180° C. holding chamber in the vapor phase of liquid nitrogen until it had reached this temperature (approximately 15 minutes). The LSE was then stored at approximately −130° C. for times ranging between 30 minutes to several days.

The thawing protocol consisted of submerging the vitrified LSE into 50% VS1+1 Molar (M) sucrose at 4.0° C. for 15 minutes, then replacing that solution with 25% VS1+1 M sucrose at room temperature for 15 minutes, then replacing the solution with DMEM+ 1 M sucrose at room temperature for 15 minutes, followed by DMEM at room temperature for 15 minutes.

This protocol achieved viability (as determined by histologic examination) only at the edges of the LSE, with a larger central area of non-viable epidermal cell. It was determined that the reason for the lack of viability was that the cryoprotectants were not effectively permeating the LSE. This lack of perfusion of the cryoprotectant was due to the increasing viscosity of the cryoprotectant solution as the temperature was decreased. At −20° C., the cryoprotectant is still a liquid, but it is quite viscous.

II. Freezing LSE with Cryopreservation Method

A. To enhance viability, the foregoing was repeated utilizing the present method wherein LSE was centrifuged for 5 to 15 minutes during the final or 100% VS1 perfusion step. This approach resulted in a striking improvement with nearly 100% viability, as measured by MTT conversion. Gay et al., "The Living Skin Equivalent as a Model In Vitro for Ranking the Toxic Potential of Dermal Irritants," *Toxic. in Vitro*, 6:303–315 (1992).

Morphologically, little or no difference between frozen and non-frozen LSE was observed. Though there did appear to be some variability among samples, it was noted that when a sample was not properly vitrified its morphologic appearance after thawing showed totally non-viable cells. Due to the impractical scale-up nature of centrifugation, agitation on a shaker platform in a −20° C. freezer was explored next as a means of enhancing perfusion. This type of agitation gave results similar to those observed using centrifugation as the agitation method.

B. In this experiment a vitrification solution was employed which did not contain the potentially carcinogenic compound, acetamide (W.F. Rail, *Cryobiology*, 24:387–404 (1987)). A new vitrification solution containing 65% glycerol in DMEM+0.3% NCS (full strength) was evaluated. Both the step-wise addition procedure the thawing protocol were the same as described above with the modified VS1: Dilutions of the full strength solution were made with base media to achieve 50% and 25% strength solutions. The step wise addition protocol was as follows: LSE was immersed in 25% solution room temperature for 15 minutes, then replaced with 50% solution at 4.0° C. for 15 minutes, then replaced with 100% solution at −20° C. for 15 to 20 minutes. The LSE was then placed into a −180° C. holding chamber in the vapor phase of liquid nitrogen until it had reached this temperature (approximately 15 minutes). The LSE was then stored at approximately −130° C. for times ranging between 30 minutes to several days. To thaw, the vitrified LSE was submerged into 50% solution+1 Molar (M) sucrose at 4.0° C. for 15 minutes, then that solution was replaced with 25% solution+1 M sucrose at room temperature for 5 minutes, then that solution was replaced with DMEM+1 M sucrose room temperature for 15 minutes, followed by DMEM at room temperature for 15 minutes.

Figure 1B:
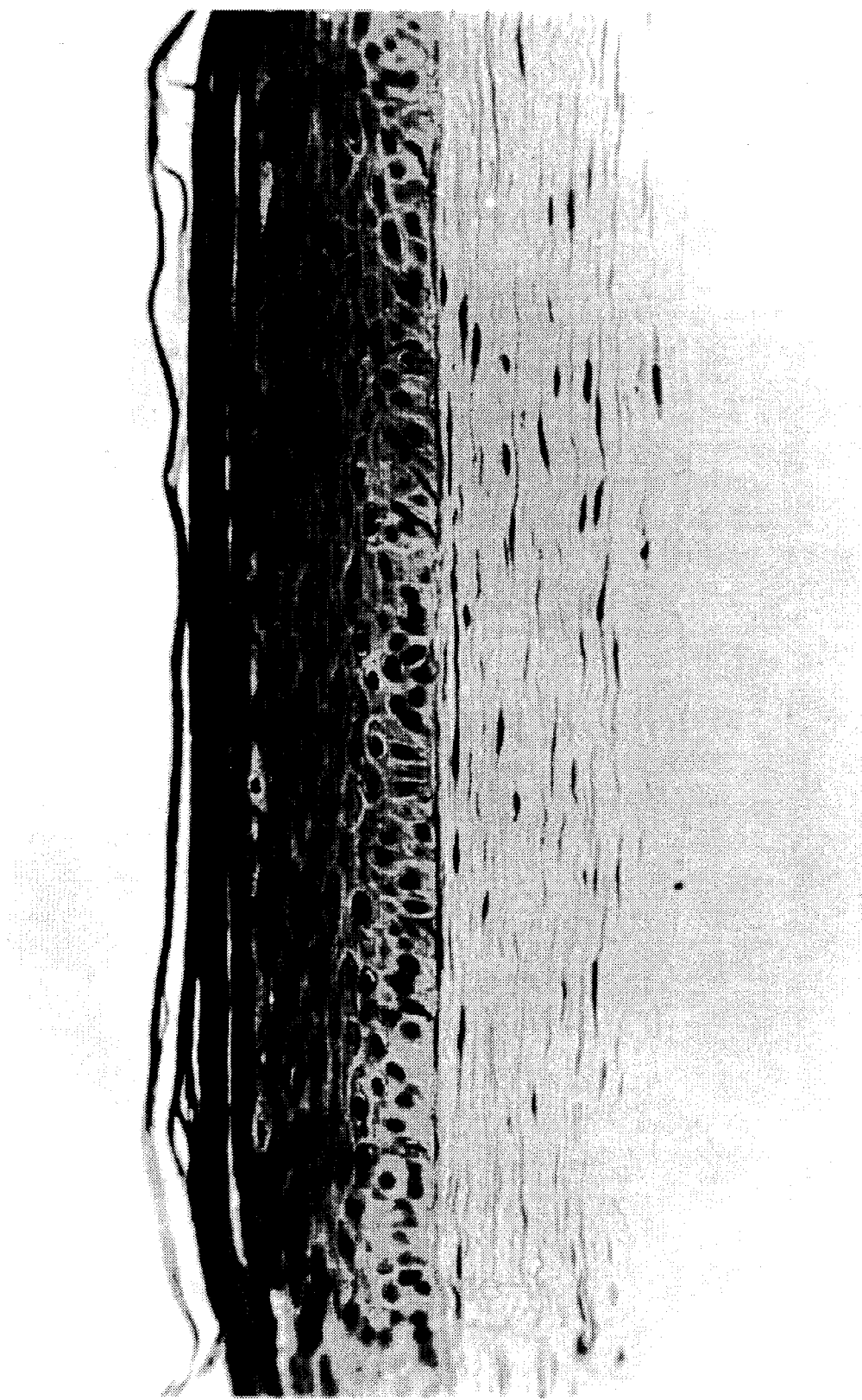

This protocol gave consistently higher levels of viability than with the modified VS1. This solution also decreased the level of variability; the cryopreserved LSEs were consistently more viable. Morphologically there was no apparent difference in appearance between the frozen and non-frozen LSE as shown in FIG. 1. The viability was estimated to approach 100% by histologic examination and by the MTT assays as shown by FIG. 2. Toxicity of the glycerol cryoprotectant during agitation was tested at various lengths exposure time from 5 minutes to 40 minutes, with the preferable range for minimum toxicity at 10 to 15 minutes.

C. In this experiment larger sizes of LSE were evaluated. It was observed that variability in viability could be reduced by increasing the surface area of LSE in close contact with the warming solution during the thaw procedure. This was accomplished by drawing a vacuum within a protective pouch containing the perfused LSE prior to the final freezing step, thus minimizing insulation of air between the LSE and the surrounding protective pouch. This procedure resulted in a much greater warming rate of the tissue, and increased the cellular viability of the LSE, particularly the fibroblasts. The fibroblasts appeared to be more susceptible to devitrification (the formation of ice during warming) than the epidermal cells.

Figure 2A:
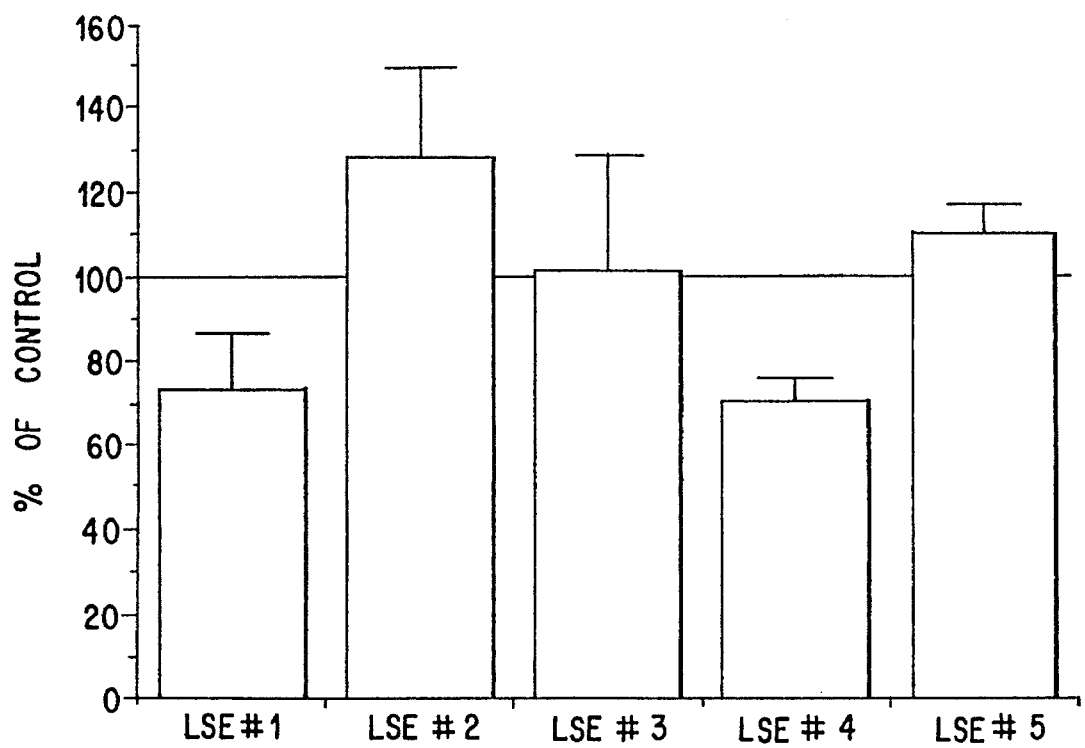
FIG. 2(A) is LSEs cryopreserved for 0.5 to 1.0 hour then rapidly thawed and incubated for 24 hours in a 10% $CO_2$ 37° C. incubator. Viability was measured by MTT analysis of three 0.5 $cm^2$ punches of a 44 $cm^2$ sample.
Figure 2B:
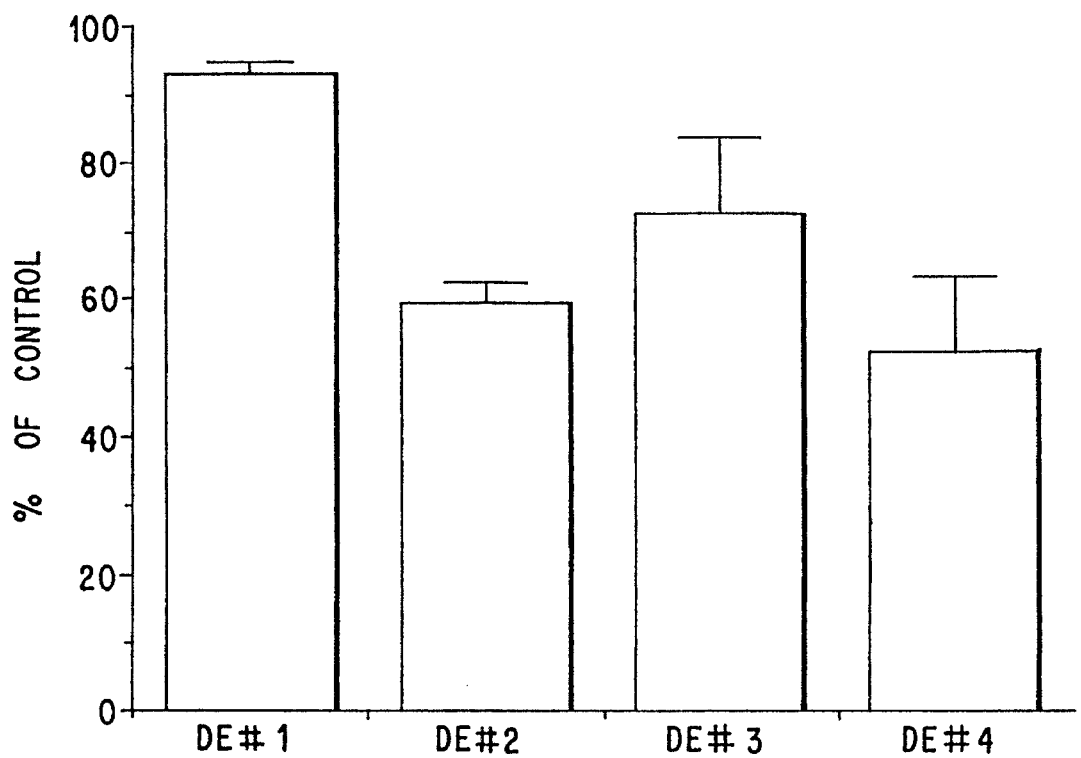
FIG. 2(B) is the dermal portion of LSE with the epidermal layer removed postcryopreservation to assay fibroblast viability. Viability was measured by MTT analysis of three 0.5 cm² punches of a 44 cm² sample.

Thawed LSE were incubated for one day in medium at 37° C. before assessing the viability of each layer using the MTT viability assay and routine histology. LSE rapidly frozen by the present method and using 65% glycerol showed good viability after 1 day post-thaw as can be seen in FIG. 2(A). Because the cell densities between the epidermal and dermal layers were very different, the dermal layers (DE) of the frozen LSE were also measured separately (FIG. 2(B)). Both layers showed good viability and maintenance of morphology as shown in FIG. 3.

Cell viability was measured using the MTT assay, a colorimetric MTT conversion assay developed to measure cellular growth and viability. This assay is described in detail in Gay et al., "The Living Skin Equivalent as a Model In Vitro for Ranking the Toxic Potential of Dermal Irritants," *Toxic. in Vitro*, 6:303–315 (1992). The metabolic reduction of the soluble tetrazolium salt to a blue formazan precipitate is dependent on the presence of viable cells with intact mitochondrial function. This assay is used to quantitate cytotoxicity in a variety of cell types, including cultured human keratinocytes. 1.5 ml of LSE assay medium containing 0.33 mg MTT/ml (Sigma Chemical Co., St. Louis, Mo.) was added to each well. LSE were incubated in the MTT-containing assay medium for 3–4 hours. At the end of the conversion period the exposed portion of the LSE was excised using an 8-mm diameter skin biopsy punch and extracted for 2–24 hours at room temperature in 0.3 ml isopropanol, acidified with 0.04 N HCl. At the end of the extraction period, 0.2 ml of each extract was transferred to a well of a 96 well plate and the absorbance at 570 nm was read on a plate reader (Dynatech), with the isopropanol extraction medium as a blank. For the LSE, the total MTT conversion reported is the sum of the combined metabolic activities of fibroblasts and keratinocytes in the LSE. By stripping the epidermis away from the dermis after MTT staining, the relative contributions of the fibroblasts in the dermal layer and of the keratinocytes in the epidermis were determined.

III. Grafting LSE onto Athymic Mice

Freshly thawed LSEs, after cryopreservation as described above, with no post-thaw incubation, were grafted onto athymic mice to determine any change in graft performance, i.e., any change in the rate of graft take, evidence of short term damage, or any change in long term persistence.

Figure 3A:
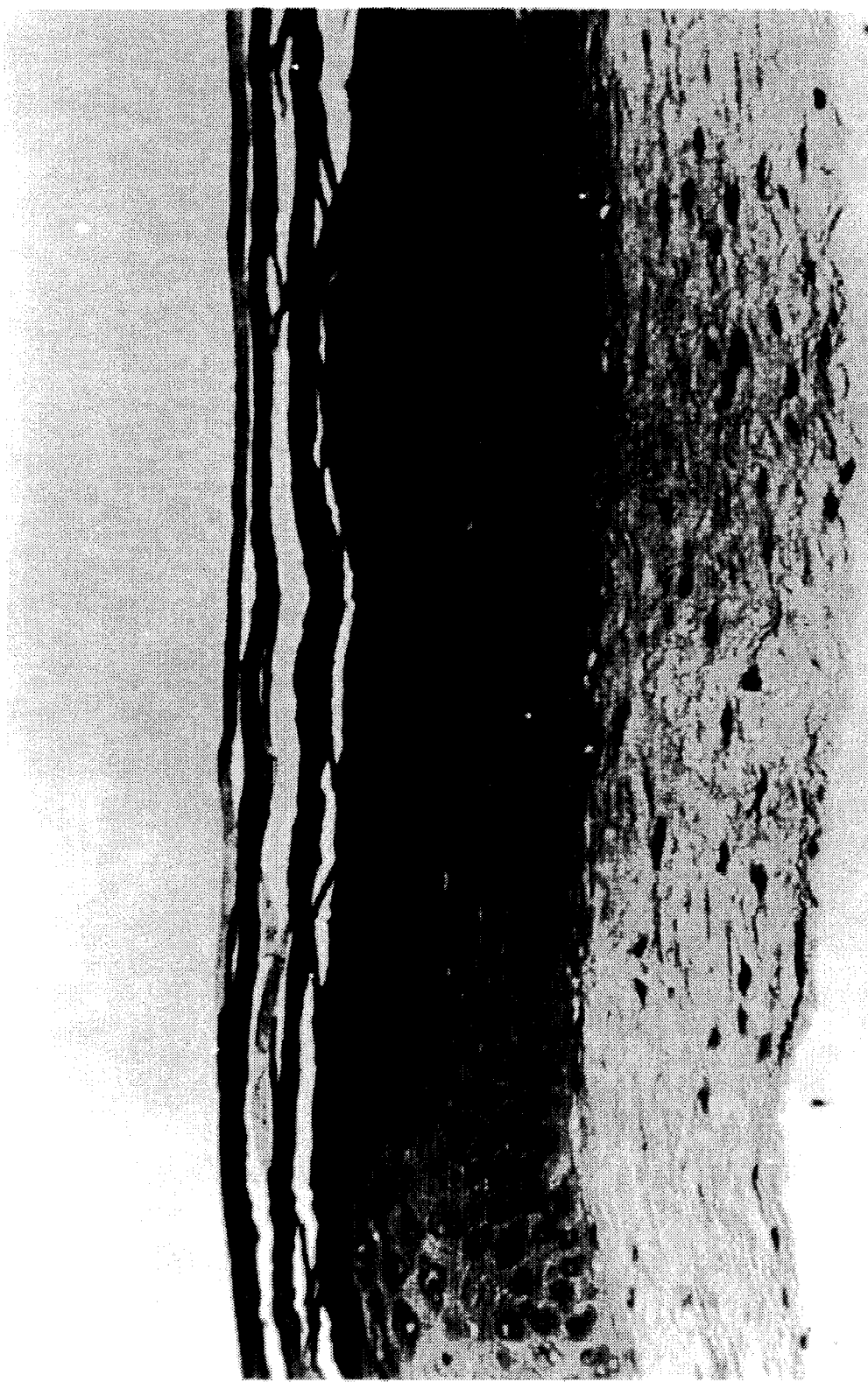
FIGS. 3(A), 3(B), and 3(C) show the time sequence of LSE pre- and post-grafting onto 2×2 cm full-thickness wounds of athymic mice shown in light micrograph (H&E) sections of biopsied tissue. LSE grafts were frozen and stored 72 hours prior to thaw and same-day application.

The morphology of the control non-frozen, non-grafted LSE is shown in FIG. 3(A).

Figure 3B:
Figure 3C:

Post-graft examinations of the thawed LSEs at 6 days and 30 days are shown in FIGS. 3(B) and 3(C), respectively. The six day grafts showed no sign of degeneration or focal necrosis. The thirty day grafts showed comparable epidermal persistence, and vascularization of the dermal matrix. Additionally, there was no difference between control, non-frozen LSE in graft take and the thawed LSE in graft take as indicated by morphology comparisons (data not shown).

Although the foregoing invention has been described in some detail by way of illustration and example for purposes of clarity of understanding, it will be obvious to one skilled in the art that certain changes and modifications may be practiced within the scope of the invention, as limited only by the scope of the appended claims.

What is claimed is:

1. A method for vitrifying a cultured skin or cornea equivalent, comprising:
    (a) serially immersing said cultured skin or cornea equivalent in a series of cryoprotectant solutions which increase in concentration and decrease in temperature to produce a cryoprotected cultured skin or cornea equivalent;
    (b) cooling said cryoprotected cultured skin or cornea equivalent to a temperature at or below $-110°$ C., at a cooling rate at $-10°$ C. per minute or faster to produce a vitrified cultured skin or cornea equivalent; and
    (c) storing said vitrified cultured skin or cornea equivalent at a temperature of $-110°$ C. or below to produce a stored cultured skin or cornea equivalent,
    wherein one or more members of said series of cryoprotectant solutions of step (a) which increase in concentration and decrease in temperature containing the immersed cultured skin or cornea equivalent is agitated under conditions sufficient to achieve effective penetration of said cryoprotectant solution into said cultured skin or cornea equivalent prior to storage.

2. A method for vitrifying a cultured skin or cornea equivalent, comprising:
    (a) serially immersing said cultured skin or cornea equivalent in a series of cryoprotectant solutions which increase in concentration and decrease in temperature to produce a cryoprotected cultured skin or cornea equivalent at a final temperature of from $-10°$ C. to $-30°$ C.;
    (b) cooling said cryoprotected cultured skin or cornea equivalent to a temperature at or below $-110°$ C. at a cooling rate at of $-10°$ C. per minute or faster to produce a vitrified cultured skin or cornea equivalent; and
    (c) storing said vitrified cultured skin or cornea equivalent at a temperature of $-110°$ C. or below to produce a stored cultured skin or cornea equivalent,
    wherein one or more members of said series of cryoprotectant solutions of step (a) which increase in concentration and decrease in temperature containing the immersed cultured skin or cornea equivalent is agitated under conditions sufficient to achieve effective penetration of said cryoprotectant solution into said cultured skin or cornea equivalent prior to storage.

3. A method for vitrifying a cultured skin or cornea equivalent, comprising:
    (a) immersing said cultured skin or cornea equivalent in a first cryoprotectant solution having a concentration of from 15% to 35% cryoprotectant solution in base media at room temperature for a period of time of from 10 to 20 minutes to produce a first cryoprotected cultured skin or cornea equivalent;
    (b) immersing said first cryoprotected cultured skin or cornea equivalent of step (a) in a second cryoprotectant solution having a concentration of from 40% to 60% cryoprotectant solution in base media at a temperature of from $10°$ C. to $-2°$ C. for a period of time of from 10 to 20 minutes to produce a second cryoprotected cultured skin or cornea equivalent;
    (c) finally immersing said second cryoprotected cultured skin or cornea equivalent of step (b) in a third cryoprotectant solution having a concentration of 100% cryoprotectant solution at a temperature of from $-10°$ C. to $-30°$ C. for a period of time of from 10 to 20 minutes to produce a third cryoprotected cultured skin or cornea equivalent;
    (d) cooling said third cryoprotected cultured skin or cornea equivalent of step (c) to a temperature at or below $-110°$ C. at a cooling rate of $-10°$ C. per minute or faster to produce a vitrified cultured skin or cornea equivalent; and
    (e) storing said vitrified cultured skin or cornea equivalent at a temperature at or below $-110°$ C. to produce a stored cultured skin or cornea equivalent,
    wherein said cultured skin or cornea equivalent of at least step (c) and said cryoprotectant solution are agitated under conditions sufficient to achieve effective penetration of said cryoprotectant solution into said cultured skin or cornea equivalent.

4. The method of any one of claims 1, 2 or 3, wherein said cryoprotectant solution comprises one or more agents selected from the group consisting of: a cell-penetrating, glass-forming agent and a non cell-penetrating, glass-forming agent.

5. The method of claim 4, wherein said non cell-penetrating, glass-forming agent is a high molecular weight form of a complex carbohydrate comprising one or more members selected from the group consisting of: chondroitin sulfate, polyvinylpyrrolidone, and polyethylene glycol.

6. The method of claim 4, wherein said non cell-penetrating, glass-forming agent is a hetastarch.

7. The method of claim 6, wherein said herastarch is hydroxyethyl starch.

8. The method of claim 4, wherein said cell-penetrating, glass-forming agent is selected from the group consisting of:

glycerol, propylene glycol, ethylene glycol, and dimethylsulfoxide.

9. The method of claim 8, wherein said cell-penetrating, glass-forming agent is glycerol.

10. The method of any one of claims 1, 2, or 3, wherein said stored skin or cornea equivalent of step (c) is stored in liquid nitrogen at a temperature of −196° C.

11. The method of claim 3, wherein said cryoprotectant solution having a concentration of 100% comprises a member selected from the group consisting of: 65% glycerol in Dulbecco's modified Eagles' medium+0.3% newborn calf serum; 20.5% dimethylsulfoxide+15.5% acetamide+10% propylene glycol+6% polyethylene glycol in a base of 0.3% newborn calf serum in Dulbecco's modified Eagles' medium, wherein said cryoprotectant solution having a concentration of 100% is diluted with base media to produce the cryoprotectant solutions of step (a) and step (b).

12. The method of any one of claims 1, 2 or 3, further comprising: thawing said stored cultured tissue equivalent at a rate effective to produce a thawed viable cultured tissue equivalent.

13. The method of claim 12, further comprising: rinsing said thawed viable cryopreserved cultured tissue equivalent with an isotonic solution buffered at physiological pH.

14. The method of claim 13, wherein said isotonic solution comprises 0.5 to 2.0 M sucrose.

15. The method of any one of claims 1, 2 or 3, wherein said cooling rate is from −10° C. per minute to −30° C. per minute.

16. The method of any one of claims 1, 2 or 3, wherein said cultured tissue equivalent is sterilely vacuum sealed in a protective pouch prior to said step of cooling.

* * * * *